United States Patent [19]

Pert et al.

[11] Patent Number: 5,863,718
[45] Date of Patent: Jan. 26, 1999

[54] SMALL PEPTIDES WHICH INHIBIT TO T-4 RECEPTORS AND ACT AS IMMUNOGENS

[75] Inventors: Candance B. Pert; Michael R. Ruff, both of Bethesda; William L. Farrar, Gaithersburg, all of Md.

[73] Assignee: The United States of America as represented by the Department of Health and Human Services, Washington, D.C.

[21] Appl. No.: 486,678

[22] Filed: Jun. 7, 1995

Related U.S. Application Data

[60] Continuation of Ser. No. 105,926, Aug. 13, 1993, which is a division of Ser. No. 568,616, Aug. 16, 1990, Pat. No. 5,276,016, which is a continuation of Ser. No. 314,507, Feb. 15, 1989, abandoned, which is a continuation of Ser. No. 48,148, May 11, 1987, abandoned, which is a continuation-in-part of Ser. No. 878,586, Jun. 26, 1986, abandoned, which is a continuation-in-part of Ser. No. 869,919, Jun. 3, 1986, abandoned.

[51] Int. Cl.$^6$ .......................... C12Q 1/70; G01N 33/53; A61K 38/04; C07K 5/00
[52] U.S. Cl. ............................. 435/5; 435/7.1; 435/7.2; 530/324; 530/325; 530/329; 530/326; 530/330; 514/15; 424/208.1
[58] Field of Search .................................. 435/5, 7.1, 7.2; 530/324, 325, 326, 329, 330; 424/208.1; 514/15

[56] References Cited

U.S. PATENT DOCUMENTS

| | | | |
|---|---|---|---|
| 4,073,885 | 2/1978 | Pert et al. | 424/101 |
| 4,371,463 | 2/1983 | Pert et al. | 260/112.5 |
| 4,520,113 | 5/1985 | Callo et al. | 436/504 |
| 4,525,300 | 6/1985 | Yoshida et al. | 260/112.5 |
| 4,629,783 | 12/1986 | Cosand | 530/324 |
| 4,737,487 | 4/1988 | Watts et al. | 514/15 |
| 4,775,759 | 10/1988 | Rice et al. | 546/44 |
| 4,956,273 | 9/1990 | Kennedy et al. | 435/5 |
| 5,276,016 | 1/1994 | Pert et al. | 514/15 |
| 5,529,983 | 6/1996 | Pert et al. | 514/16 |

OTHER PUBLICATIONS

Wetterberg, et al, 1987, "Peptide T in the treatment of AIDS". The Lancet, Jan. 17, 1987, p. 159.
The Lancet, Jan. 17, 1987, Hepatotoxicity of Cyclosporin in a Patient Given Nordette.
The Lancet, Boston Mass. and London Saturday Jul. 22, 1989 vol. II for 1989.
MacFadden, D.K.*, Doob, Penelope Reed *.** Role of Peptide T in Palliation of HIV–1–Related Painful Peripheral Neuropathy.
Douglass E. Brenneman, et al., Acquired Immune Deficiency Syndrome and the Developing Nervous System.
Phase I Studies of Peptide T for the Neuropsychiatric Complications of HIV Infection, Immunology Virology Pharmacokinetics.
Investigator's Brochure, D–Ala 1–Peptide–T–Amide, (Peptide T) Integra Institute, Bethesda, Maryland.
I. Julander, et al., Treatment of HIV–1 Infected Patients with Peptide T. Published Jan. 1991.
Abstracts of Peptide T Clinical Results, Vth International Conference on AIDS, Montreal Jun. 4–9, 1989.
Manuscripts Concerning Peptide T Clinical Results Submitted and in Press. Michael R. Ruff et al., Pharmacokinetics of Peptide T in Patients with Acquired Immunodeficiency Syndrome (AIDS).
Kenneth Mayer, M.D., et al., A Phase I Study of Intranasal Peptide T for the Treatment of Symptomatic HIV–Infected Patients: Clinical and Laboratory Results. Running Head: Intranasal Peptide T in HIV Infection.
Jeanine Buzy, et al., Potent Neurotoxic Activity in the Cerebrospinal Fluid of HIV–Infected Individuals.
T. Peter Bridge, M.D. et al., Neuropsychiatric Outcome in HIV Dementia to Peptide T.
T. Peter Bridge, M.D. et al., Results of Extended Peptide T Administration in Aids and ARC Patients.
Marc. I. Rosen, et al., Peptide T Treatment of Cognitive Impairment In HIV+ Intravenous Drug Uners.
Peter Bridge, M.D. et al.,Neuropsychologic Results of Controlled Trial of Peptide T in HIV–1.
Virology Report. Pharmacology of Peptide T inhibition of in vitro HIV infection.

(List continued on next page.)

Primary Examiner—Lynette F. Smith
Attorney, Agent, or Firm—McAulay, Fisher, Nissen, Goldberg & Kiel, LLP

[57] ABSTRACT

Short peptide of the formula:

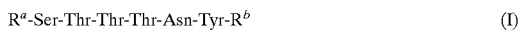

$$R^a\text{-Ser-Thr-Thr-Thr-Asn-Tyr-}R^b \quad\quad (I)$$

where $R^a$ represents an amino terminal residue Ala- or D-Ala and $R^b$ represents a carboxy terminal residue -Thr or -Thr amide or a derivative thereof with an additional Cys-residue at one or both of the amino and carboxy terminals, or a peptide of formula (II):

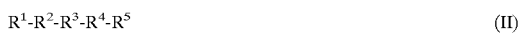

$$R^1\text{-}R^2\text{-}R^3\text{-}R^4\text{-}R^5 \quad\quad (II)$$

where $R^1$ is an amino terminal residue Thr-, Ser-, Asn-, Leu-, Ile-, Arg- or Glu-
$R^2$ is Thr, Ser or Asp
$R^3$ is Thr, Ser, Asn, Arg, Gln, Lys or Trp
$R^4$ is Tyr
and $R^5$ is a carboxy terminal amino group or a derivative thereof with a corresponding D- amino acid as the amino terminal residue, and/or a corresponding amide derivative at the carboxy terminal residue and/or additionally a Cys-residue at one or both of the amino and carboxy terminals, or a physiologically acceptable salt thereof.

Such peptides bind to T4 receptors are useful in preventing viral infectivity by viruses which bind to the T4 receptors. These peptides are believed to act as completitive blocking agents.

6 Claims, 3 Drawing Sheets

OTHER PUBLICATIONS

Peptide T Clinical Reports. Clinical Summary A Phase I Trial of Intranasal Peptide T: Safety, Toxicity and Pharmacokinetics in Human Immunodeficiency Virus 1 (HIV–1) Infected Patents.

Appendix I: Preliminary studies.

Appendex II. Neuropsychological Assessment.

AZT, AZT Placebo, and Peptide T, Neuropsychologic Test Z Scores AIDS and ARC Patients.

Fenway Clinic Trail EEG Report.

Peptide T Clinical Trials 1987–1988, NIMH/USC, Los Angeles.

Peptide T Clinical Trials 1986–1987, Karolinska Institute.

Neuropsychologic Testing Results Fenway Community Health Center Phase One Study Peptide T, IND. BB–2535 29 Oct. 9.

Angus G. Dalgleish et al. The CD4 (T4) antigen is an essential component of the receptor for the AIDS retrovirus. Nature, vol. 312, 20/27, Dec. 1984.

Bruno R. Starcich, et al. Identification and Characterization of Conserved and Variable Regions in the Envelope Gene of HTLV–III/LAV, the Retrovirus of AIDS.

Ratner, et al. Complete nucleotide sequence of the AIDS virus, HTLV–III.

Ray Sanchez–Pescador et al. Nucleotide Sequence and Expression of an AID–Associated Retrovirus (ARV–2), Science, vol. 227: pp. 484–492 (1985).

Candace B. Pert, Octapeptides deduced from the neuropeptide receptor–like pattern of antigen T4 in brain potently inhibit human immunodeficiency virus receptor binding and T–cell infectivity, Proc. Natl. Acad. Sci. USA, vol. 83, pp. 9254–9258, Dec. 1986.

J. A. Parsons, Biological Council, The Co–ordinating Committee for Symposia on Drug Action, Peptide Hormones, Jun. 1976.

Anthony S. Fauci, Current Issues in Developing a Strategy for Dealing with the Acquired Immunodefiency Syndrome, Proc. Natl. Acad. Sci. USA, vol. 83, pp. 9278–9283, Dec. 1986.

Edward S. Golub, The Cellular Basis of the Immune Response, an approach to Immunobiology. Sinaurer Associates, Inc., Sunderland, MA.

Donald J. Cram, Organic Chemistry. McGraw–Hill Book Company, 1964.

Albert L. Lehninger, Principles of Biochemistry. The Johns Hopkins University, School of Medicine, Worth Publishers, Inc. 1982.

The Spectrum of Disease due to Human Immunodeficiency Virus, by Donna Mildvan, Current Topics in AIDS, vol. 1., pp. 31–45, 1987.

Human Immunodeficiency Virus and Related Viruses, by Myra O. McClure and Robin A. Weiss, Current Topics in AIDS, vol. 1, pp. 95–117, 1987.

Michael R. Ruff et al. CD4 Receptor binding peptides that block HIV Infectivity cause human monocyte chemotaxis, FEB Letters, vol. 211, No. 1, pp. 17–22. Jan. 1987.

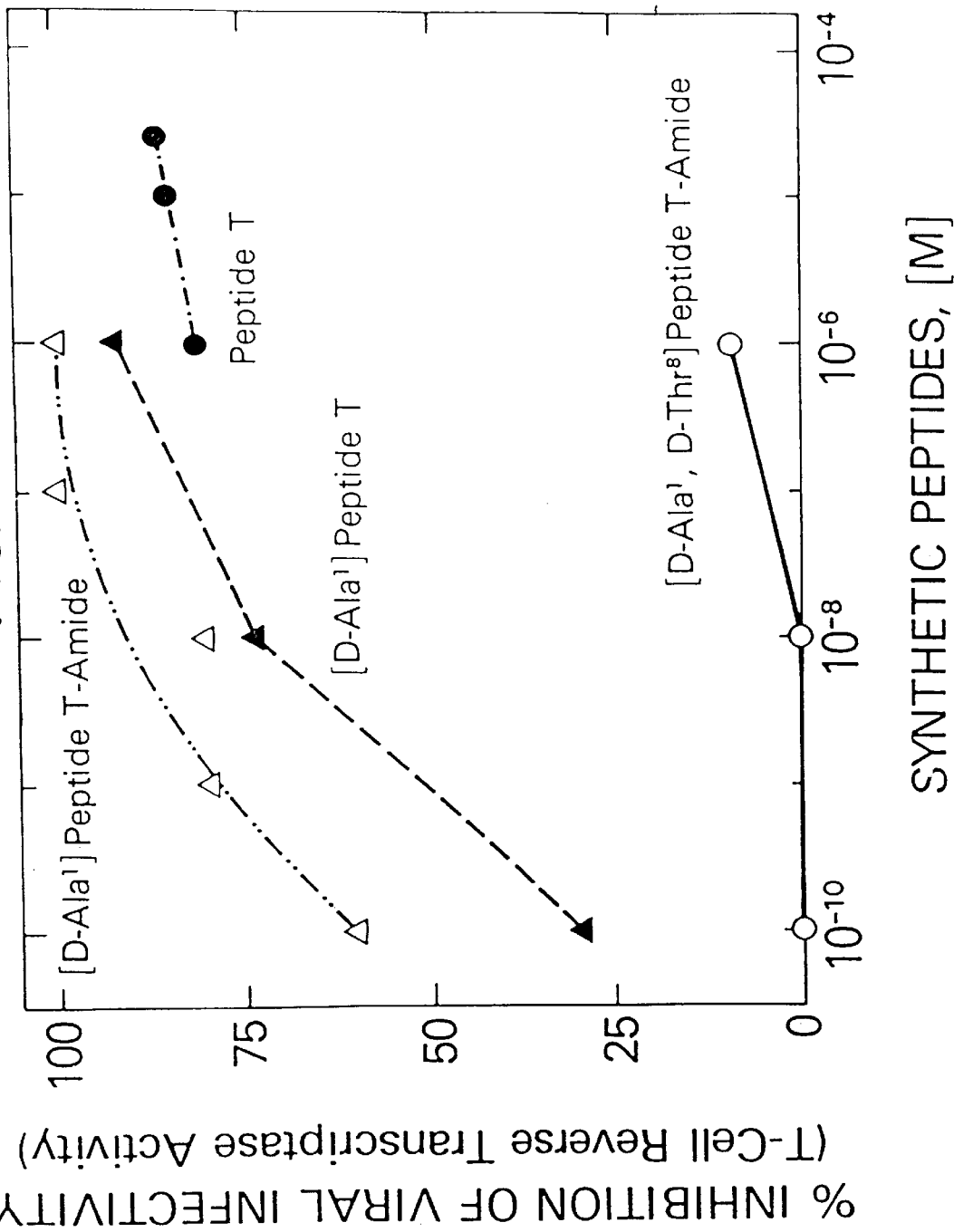

SMALL PEPTIDES WHICH INHIBIT TO T-4 RECEPTORS AND ACT AS IMMUNOGENS

This application is a Continuation of application Ser. No. 07/105,926, filed Aug. 13, 1993, pending; which is a Divisional of Ser. No. 07/568,616, filed Aug. 16, 1990, now U.S. Pat. No. 5,276,016; which is a Continuation of Ser. No. 07/314,507, filed Feb. 15, 1989, now abandoned; which is a Continuation of Ser. No. 07/048,148, filed May 11, 1987, now abandoned; which is a Continuation in Part of Ser. No. 06/878,856, filed Jun. 26, 1986, now abandoned; which is a Continuation in Part of Ser. No. 06/869,919, filed Jun. 3, 1986, now abandoned.

BRIEF DESCRIPTION OF THE INVENTION

This invention relates to synthetically produced short peptide sequences which inhibit HTLV-III/LAV (hereinafter referred to as HIV) binding to human cells by blocking receptor cites on the cell surface, and thus preventing viral infectivity of human T cell. The peptides, while preventing infectivity, also induce antibody production against the envelope protein of the HIV virus. Hence, these peptides also have use as vaccines to prevent development of Acquired Immune Disease Syndrome (AIDS). Monoclonal antibodies to the peptides could also be used as diagnostic agents to identify the HIV virus. Hence, peptides and antibodies to the peptides would have use in preparing test kits for identification of HIV carriers or persons suffering from AIDS.

BACKGROUND OF THE INVENTION

The complete nucleotide sequence of the AIDS (HIV) virus has been reported by several investigators. (See Lee Ratner et al., *Nature* 313, p. 277, January 1985; Muesing et al., *Nature* 313, p. 450, February 1985; and Wain-Habson et al., *Cell* 40, pp. 9–17, January 1985.) The envelope gene has been-associated particularly with antigenicity and infectivity. However, the envelope portion is also known to have regions which are highly divergent. The HIV virus envelope glycoprotein has been shown to affix covalently to the brain membranes of humans, rats, and monkeys and to cells of the immune system.

The realization that viruses may exert cell and tissue tropism by attachment at highly specific sites on cell membrane receptors has encouraged investigators to seek agents which would bind at the viral receptor sites of cell membranes and thus prevent binding of a specific virus to these cells. A demonstration of specific receptor-mediated vaccinia virus infectivity being blocked by synthetic peptides has been previously demonstrated (Epstein et al., *Nature* 318: 663–667)., The HIV virus has been shown to bind to a surface molecule known as the CD4 or T4 region, which is present on various cells susceptable to HIV infection, including T lymphocytes and macrophages. (See Shaw et al., *Science* 226, pp. 1165–1171 for a discussion of tropism of HTLV-III.)

In addition to symptoms arising from immunodeficiency, patients with AIDS show neuropsychological defects. The central nervous and immune systems share a large number of specific cell-surface recognition molecules, serving as receptors for neuropeptide-mediated intercellular communication. The neuropeptides and their receptors show profound evolutionary stability, being highly conserved in largely unaltered form in unicellular organisms as well as higher animals. Furthermore, the central nervous and immune systems show common DC4 (T4) cell-surface recognition molecules which serve as receptors for the binding of HIV envelope glycoprotein (gp 120). Since the same highly conserved neuropeptide informational substances integrate immune and brain function through receptors remarkably similar to those of HIV, we postulated a very similar amino acid sequence between the HIV glycoprotein gp 120 and a short peptide previously identified in another context from the envelope region of the Epstein Barr-Virus might indicate the core peptide essential for viral receptor binding. It was postulated that such a peptide would be useful in preventing infection of cells with the HIV by binding with receptor cells and blocking the binding of HIV gp 120, that such peptides binding to the receptor cites would give rise to production of antibodies directed to the peptide sequence, and that these peptides might be used to provide immunological basis for prevention of AIDS.

PURPOSE

It was the object of the present invention to provide peptides that would act to alleviate symptoms of AIDS by preventing binding of HIV (AIDS virus) to receptor sites of cells of brain membranes and the immune system.

It was also an object of the present invention to provide peptides for use as vaccines to be used to give rise to antibodies that would protect against development of AIDS in persons who might become exposed to the HIV (AIDS virus).

It was a further object of the present invention to provide diagnostic means of identifying presence of antibodies to HIV or HIV envelope protein.

DETAILED DESCRIPTION OF THE INVENTION

An octapeptide in the HIV envelope glycoprotein (gp 120) was identified by computer-assisted analysis. This peptide, termed "peptide T" because of the high threonine content, has been shown to inhibit binding of gp 120 to the brain membranes. The peptide has the sequence Ala-Ser-Thr-Thr-Thr-Asn-Tyr-Thr. Later analysis disclosed a class of related pentapeptides having similar binding properties.

According to a first aspect of the present invention there is provided a peptide of formula (I):

$$R^a\text{-Ser-Thr-Thr-Thr-Asn-Tyr-}R^b \quad (I)$$

where $R^a$ represents an amino terminal residue Ala- or D-Ala and $R^b$ represents a carboxy terminal residue -Thr or -Thr amide or a derivative thereof with an additional Cys-residue at one or both of the amino and carboxy terminals, or a peptide of formula (II):

$$R^1\text{-}R^2\text{-}R^3\text{-}R^4\text{-}R^5 \quad (II)$$

where $R^1$ is an amino terminal residue Thr-, Ser-, Asn-, Glu-, Arg-, Ile- or Leu-, $R^2$ is Thr, Ser or Asp, $R^3$ is Thr, Ser, Asn, Arg, Gln, Lys or Trp $R^4$ is Tyr and $R^5$ is preferably a carboxy terminal residue -Thr, -Arg or -Gly or a derivative thereof with a corresponding D-amino acid as the amino terminal residue, and/or a corresponding amide derivative at the carboxy terminal residue and/or additionally a Cys- residue at one or both of the amino and carboxy terminals. While the preferred amino acids at $R^5$ have been designated, it is known the amino acid at this position may vary widely. In fact, it is possible to terminate the peptide with $R^4$ (Tyrosine) as the carboxy terminal amino acid wherein $R^5$ is absent. Such peptides retain the binding properties of the group taught herein. Serine and threonine appear to be interchangeable for purposes of biological properties taught herein. The active compounds of the invention may exist as physiologically acceptable salts of the peptides.

This class of peptides has been found to bind to the T4 viral receptors.

Most preferred peptides, as well as peptide T above, are the following octapeptides of formula (I):
D-Ala-Ser-Thr-Thr-Thr-Asn-Tyr-Thr and D-Ala-Ser-Thr-Thr-Thr-Asn-Tyr-Thr-amide and the following pentapeptides of formular (II):
Thr-Asp-Asn-Tyr-Thr
Thr-Thr-Ser-Tyr-Thr
Thr-Thr-Asn-Tyr-Thr
and their analogues with D-Thr as the amino terminal residue and/or an amide derivate at the carboxy terminal.

The compounds of the invention may be beneficially modified by methods known to enhance passage of molecules across the blood-brain barrier. Acetylation has proven to be especially useful for enhancing binding activity of the peptide. The terminal amino and carboxy sites are particularly preferred sites for modification.

The peptides of this invention may also be modified in a constraining conformation to provide improved stability and oral availability.

The following abbreviations are used hereinafter:

| Amino Acid | Three Letter Code | One Letter Code |
| --- | --- | --- |
| arginine | arg | R |
| asparagine | asn | N |
| aspartic acid | asp | D |
| cysteine | cys | C |
| glycine | gly | G |
| serine | ser | S |
| threonine | thr | T |
| tyrosine | tyr | Y |

Unless otherwise indicated the amino acids are, of course, in the natural form of L-stereoisomers.

A comparison of amino acid sequences of 12 pentapeptides is presented in Table 1. Although historically our initial computer search revealed peptide T (contained in the ARV isolate) to be the relevant moiety, as additional viral sequences became available it become clear that the relevant, bioactive sequence, might be a shorter pentapeptide comprising, nominally, peptide T[4–8], or the sequence TTNYT. In the isolates we compared (Table 1) substantial homologies were discerned only in this, shorter, region. The majority of changes are the interconversions of serine (S) and threonine (T), two closely related amino acids. The tyrosine of position 7 of peptide T is an invariant feature of all these constructs indicating that it may be obligatory for bioactivity. Substitutions occurring at position 5 include T, G, R or S. Position 4 and 6 were first restricted (with one exception) to S, T and N, all amino acids containing uncharged polar groups with closely similar steric properties. An assessment of general sequence concordance among 5 various AIDS viral isolates (9,10) reveals that the region around and including the peptide T sequence is a highly variable area. Such variability may indicate specialization through strong selective diversification of the function(s) which may be defined at this locus. Like the opiate peptides, these peptide T analogs seem to exist in multiple forms, reminiscent of met and leu enkephalin. These pentapeptide sequences represented in these various AIDS virus isolates are biologically active and capable of interacting as agonists of the CD4 receptor—previously known largely as a surface "marker" of T helper cells.

TABLE 1

Comparison of ENV Sequence from Multiple AIDS Virus Isolates

| Isolate | Sequence | Reference |
| --- | --- | --- |
| peptide T | ASTTTNYT | Pert, C. B. et al. PNAS (in press) |
| [1]ARV (195–199) | TTNYT | Willey, R. L. et al. |
| LAV | TTSYT | PNAS 83: 5038, 1986 |
| Z3 | SSTYR | |
| NY5 | NTSYT | |
| B10 (HTLV-III) | TTSYT | Starcich, B. R. et al. |
| WMJ-1 | SSTYR | Cell 45: 637, 1986 |
| HAT-3 | NTSYG | |
| Sequential isolates | STNYR | |
| WMJ-1 | SSTYR | Hahn, B. L. et al. |
| WMJ-2 | SSRYR | Science 232: 1548, |
| WMJ-3 | SSTYR | 1986 |
| | TTSYS | |

[1]Numbers refer to relative positions of amino acids within the ARV env sequence (9).

The seven amino acid peptide CYS-THR-THR-ASN-TYR-THR-CYS is also active. Addition of cysteines to a core does not adversely affect activity.

The peptides were custom synthesized by Peninsula laboratories under a confidentiality agreement between the inventors and the manufacturer. The Merrifield method of solid phase peptide synthesis was used. (See U.S. Pat. No. 3,531,258 which is incorporated herein by reference.) The synthesized peptides are especially preferred. While peptide T and the pentapeptide which is a portion thereof could be isolated from the virus, the peptides prepared in accord with Merrifield are free of viral and cellular debris. Hence, untoward reactions to contaminants does not occur when the synthesized peptides are used.

The peptides of the invention may be produced by conventional methods of peptide synthesis. Both solid phase and liquid phase methods may be used. We have found the solid phase method of Merrifield to be particularly convenient. In this process the peptide is synthesized in a stepwise manner while the carboxy end of the chain is covalently attached to the insoluble support. During the intermediate synthetic stages the peptide remains in the solid phase and therefore can be conveniently manipulated. The solid support is a chloromethylated styrene-divinylbenzene copolymer.

An N-protected form of the carboxy terminal amino acid, e.g. a t-butoxycarbonyl protected (Boc-) amino acid, is reacted with the chloromethyl residue of the chloromethylated styrene divinylbenzene copolymer resin to produce a protected amino acyl derivative of the resin, where the amino acid is coupled to the resin as a benzyl ester. This is deprotected and reacted with a protected form of the next required amino acid thus producing a protected dipeptide attached to the resin. The amino acid will generally be used in activated form, e.g. by use of a carbodiimide or active ester. This sequence is repeated and the peptide chain grows one residue at a time by condensation at the amino end with the required N-protected amino acids until the required peptide has been assembled on the resin. The peptide-resin is then treated with anhydrous hydrofluoric acid to cleave the ester linking the assembled peptide to the resin, in order to liberate the required peptide. Side chain functional groups of amino acids which must be blocked during the synthetic procedure, using conventional methods, may also be simultaneously removed. Synthesis of a peptide with an amide group on its carboxy terminal can be carried out in conventional manner, using a 4-methylbenzhydrylamine resin.

The compounds of the invention were found to effectively block receptor sites of cells and to prevent cell infectivity with HIV (AIDS virus) in monkey, rat, and human brain membranes and cells of the immune system.

As an aspect of the invention, therefore, we provide a pharmaceutical composition comprising a peptide compound of the invention in association with a pharmaceutically acceptable carrier or excipient, adapted for use in human or veterinary medicine. Such compositions may be presented for use in conventional manner in admixture with one or more physiologically acceptable carriers of excipients. The compositions may optionally further contain one or more other therapeutic agents which may, if desired, be a different antiviral agent.

Thus, the peptides according to the invention may be formulated for oral, buccal, parenteral, topical or rectal administration.

In particular, the peptides according to the invention may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/ or dispersing agents. Alternatively, the active ingredient may be in powder form for constitution with a suitable vehicle, e.g. sterile, pyrogen-free water, before use.

The pharmaceutical compositions according to the invention may also contain other active ingredients such as antimicrobial agents, or preservatives.

The compositions may contain from 0.001–99% of the active material.

The invention further provides a process for preparing a pharmaceutical composition which comprises bringing a peptide of the invention into association with a pharmaceutically acceptable excipient or carrier.

For administration by injection or infusion, the daily dosage as employed for treatment of an adult human of approximately 70 kg body weight will range from 0.2 mg to 10 mg, preferably 0.5 to 5 mg, which may be administered in 1 to 4 doses, for example, depending on the route of administration and the condition of the patient.

It was postulated that the affinity constants are similar to those of morphine. On the basis of this affinity, dosage of 0.33–0.0003 mg/kg per day was suggested. This has proven to be effective. A blood concentration $10^{-6}$ to $10^{-11}$ molar blood concentration is suggested. In monkeys 3 mg/kg per day achieves a serum concentration of $150 \times 10^{-9}$M. This concentration is 15 times greater than necessary to achieve a concentration of $10^{-8}$M. Primates generally require 10 times the dose used in humans.

A further aspect of this invention relates to vaccine preparations containing a peptide according to the invention, to provide protection against infection by AIDS virus. The vaccine will contain an effective immunogenic amount of peptide, e.g. 1 μg to 20 mg/kg of host, optionally conjugated to a protein such as human serum albumin, in a suitable vehicle, e.g. sterile water, saline or buffered saline. Adjuvants may be employed, such as aluminum hydroxide gel. Administration may be by injection, e.g. intramuscularly, interperitoneally, subcutaneously or intravenously. Administration may take place once or at a plurality of times, e.g. at 1–4 week intervals.

Antigenic sequences from crab as well as proteins from other invertebrates can also be added to the peptides of the invention to promote antigenicity.

A yet further aspect of this invention relates to test kits for the detection of the AIDS virus and antibodies to the AIDS virus containing a peptide according to the invention as source of antigen, or a monoclonal antibody elicited by a peptide according to the invention. For example, a peptide according to the invention may be used in a test kit to detect AIDS infection and to diagnose AIDS and pre-AIDS conditions by using it as the test reagent in an enzyme-linked immunosorbent assay (ELISA) or an enzyme immunodot assay. Such test kits may include an insoluble porous surface or solid substrate to which the antigenic peptide or monoclonal antibody has been preabsorbed or covalently bound, such surface or substrate preferably in the form of microtiter plates or wells; test sera; heteroantisera which specifically bind to and saturate the antigen or antibody absorbed to the surface or support; various diluents and buffers; labelled conjugates for the detection of specifically bound antibodies and other signal-generating reagents such as enzyme substrates, cofactors and chromogens.

The peptide according to the invention may be used as an immunogen to elicit monoclonal antibodies which specifically bind to the relevant portion of the envelope sequence of the AIDS virus, using conventional techniques; such monoclonal antibodies form a further feature of the invention.

EXPERIMENTAL METHODS AND DATA

Radiolabeling of gp 120, Preparation of Brain Membranes, Binding and Crosslinking of gp120 to Receptor, and Immunoprecipitation of T4 Antigen. HTLV-IIIb isolate of HIV was propaged in H9 cells, and the gp120 was isolated by immunoaffinity chromatography and preparative $NaDodSO_4$/PAGE. Purified gp120 was labeled with $^{125}I$ by the chloramine-T method.

Fresh human, monkey, and rat hippocampus were quickly homogenized (Polytron, Brinkmann Instruments) in 100 vol of ice-cold 50 mM Hepes (pH 7.4). The membranes collected by centrifugation (15,000×g) were washed in the original buffer volume and were used fresh or stored at $-70°$ C. Before use, brain membranes and highly purified T cells (ref. 16; gift of Larry Wahl) were preincubated for 15–30 min in phosphate-buffered saline (PBS). Membranes derived from 2 mg (initial wet weight) of brain (100 μg of protein) were incubated with 28,000 cpm of $^{125}I$-gp120 for 1 hr at 37° C. in 200 μl (final volume) of 50 mM Hepes containing 0.1% bovine serum albumin and the peptidase inhibitors bacitracin (0.005%), aprotinin (0.005%), leupeptin (0.001%), and chymostatin (0.001%). Incubations were rapidly vacuum-filtered and counted to determine the receptor-bound material.

Immunoprecipitation. Immunoprecipitates were prepared by incubation (overnight at 4° C.) of 0.5% Triton X-100/ PBS-solubilized, lactoperoxidase/glucose oxidase/$^{125}I$-iodinated brain membranes or intact T cells with indicated mAbs at 10 μg per reaction. A solid-phase immunoabsorbant (immunobeads, Bio-Rad) was used to precipitate immune complexes prior to their resolution by $NaDodSO_4$/PAGE. Control incubations contained no primary mAb or a subclass control mAb (OKT8).

Chemical Neuroanatomy and Computer-Assisted Densitometry. Cryostat-cut 25-μm sections of fresh-frozen human, monkey, and rat brain were thaw-mounted and dried onto gelatin-coated slides, and receptors were visualized as described. Incubations, with or without antibodies (10 μg/ml) against T4, T4A, T8, and T11, were conducted overnight at 0° C. in RPMI medium, crosslinked onto their antigens, and visualized with $^{125}$I-labeled goat anti-mouse antibody. Incubations of slide-mounted tissue sections to label the antigen-receptor with $^{125}$I-gp120 were conducted in 5-ml slide carriers with (1 μM) or without unlabeled gp120 or mAb OKT4A (10 μg/ml) (Ortho Diagnostics).

Separation of T-Lymphocyte Subsets. Subsets of T cells were obtained by treatment of Percoll density-purified peripheral blood T cells with specific monoclonal antibodies (T4 or T8) at 10 μg/ml. The treated cells were then panned (21) on a plastic Petri dish that was coated with goat [F(ab')$_2$] anti-mouse immunoglobulin (Sero Lab, Eastbury, Mass.) for 30 min at 4° C. The nonadherent cells were then removed, washed, and analyzed for reactivity by flow cytometry. The separated T4 and T8 cell populations have <5% contamination of other T-cell subsets. Cells were then cultured with phytohemagglutinin (1 μg/ml) for 72 hr and exposed to HIV as described below. Infected cells were phenotypically characterized when cytotoxicity assays were performed.

Virus Infection. The HTLV-III virus used for infection was isolated from an interleukin 2 (IL-2)-dependent cultured T-cell line established from fresh AIDS patient material and passaged into HuT 78, a permissive IL-2-independent cell line.

DESCRIPTION OF THE DRAWINGS

FIG. 3 shows that viral infectivity is blocked by peptide T and its synthetic analogs. Each determination was performed in duplicate. Results represent a single experiment which was repeated three times with similar results.

EXAMPLE I

Figures 1A, 1B, 1C:
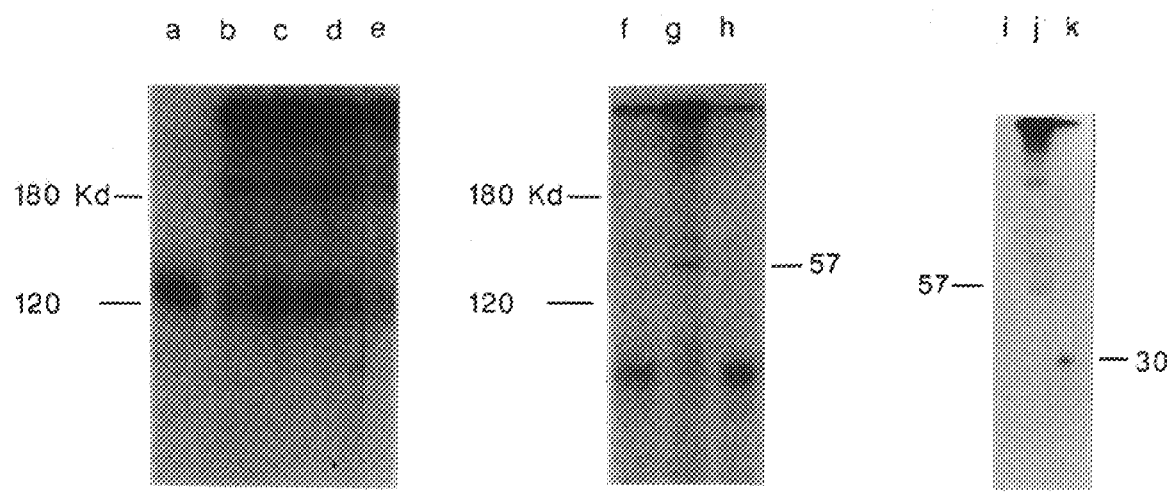
FIG. 1A shows a crosslinking of $^{125}$I-gp120 to brain membranes and T cells (a) $^{125}$I-gp120 only; (b) monkey; (c) rat; (d) human brain; and (e) human T cells.
FIGS. 1B and 1C show immunoprecipitation of $^{125}$I-labeled monkey brain membranes and human T cells, respectively; (f,i) no primary antibody control; (g,j) OKT4 Mab; (h,k) OKT8 Mab.

A single radiolabeled crosslinking product of about 180 Kd is obtained after specific binding of $^{125}$I-gp120 to membranes from either squirrel monkey, rat or human brain membranes which are indistinguishable from that of human T cells (FIG. 1A). This result indicates that gp120 can be coupled to an approximately 60 Kd protein; unreacted $^{125}$I-gp120 runs adjacent to the no membrane control (lane a).

Immunoprecipitation of radioiodinated human brain membranes with OKT4 and OKT8 (10 μg/ml) (FIG. 1B) shows that brain membranes contain a T4 antigen of about 60 Kd, indistinguishable from that identified on human T lymphocytes (FIG. 1C); by contrast, OKT8 immunoprecipitates a low (about 30 Kd) molecular weight protein from T lymphocytes (FIG. 1C) which is absent in brain membranes (FIG. 1B) indicating that brain T4 is not derived from resident lymphocytes. Similar results are observed with monkey and rat (not shown) hippocampal membranes. These results show that the T4 antigen serves as the viral receptor and is a highly conserved 60 Kd molecule shared by the immune and central nervous systems.

Figure 2:
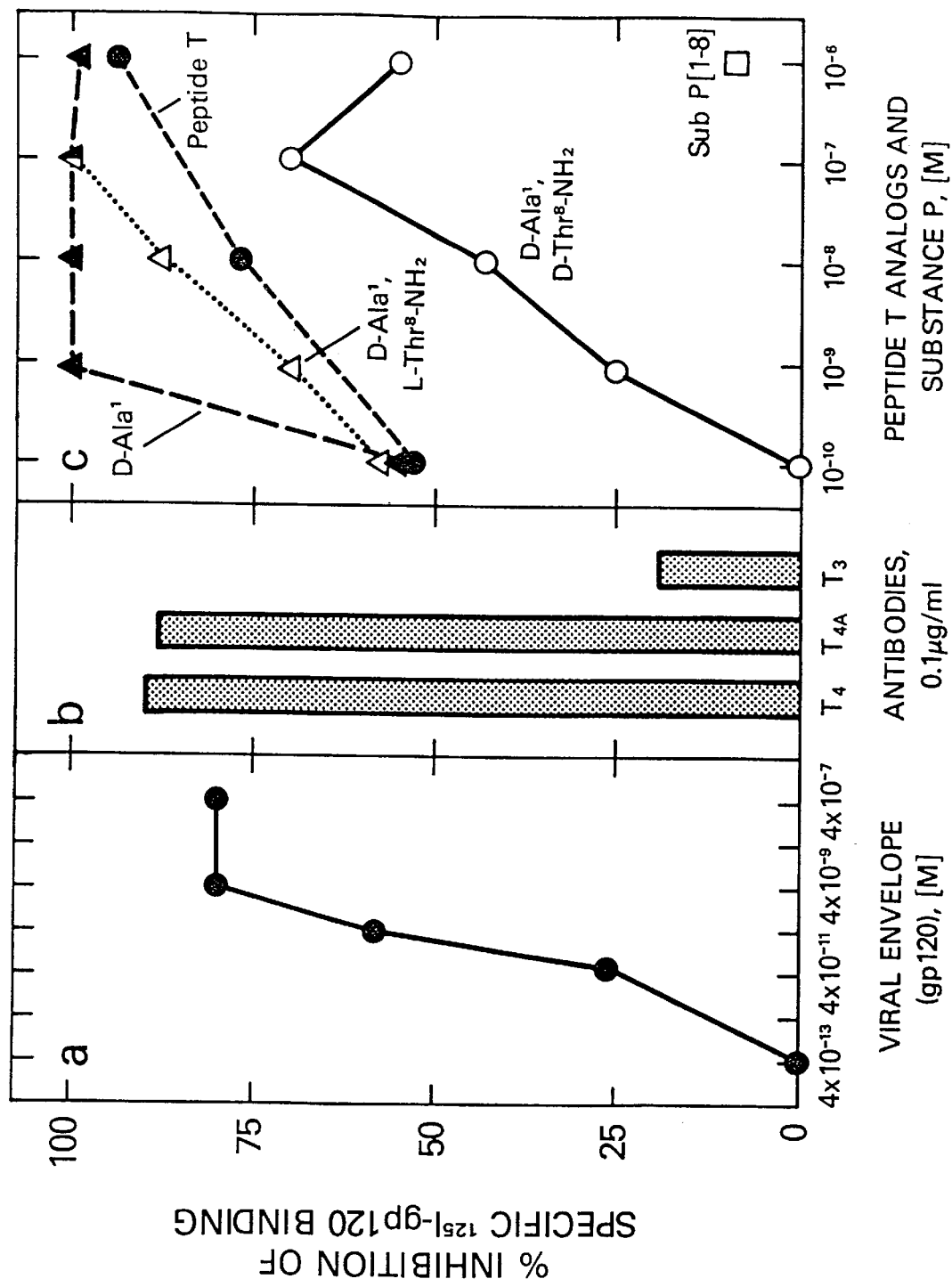
FIG. 2 shows a displacement of specific $^{125}$I-gp120 binding to fresh rat hippocampal membranes. Each determination was performed in triplicate; the results of one experiment, which was performed three times with similar results, is shown. Specific binding displaceable by 10 μg/ml of OKT4 and 4A ranged between 27 and 85% of total binding, which was 2,201+74 cpm in the experiment shown.

The realization that Epstein-Barr and HTLV-III/LAV share an almost identical octapeptide sequence caused the synthesis and study of "peptide T." FIG. 2 demonstrates the high (0.1 nM range) affinity and saturability (FIG. 2A of $^{125}$I-gp120 binding to freshly prepared rat brain membranes. Specificity (FIG. 2B) is demonstrated by blockade with OKT4 and OKT4A, but not OKT3 (0.1 μg/ml). Peptide T and two of its synthetic analogs (but not the irrelevant octapeptide substance P [1–8]) significantly inhibited $^{125}$I-gp120 binding in the 0.1 nM range (FIG. 2C). Substitution of a D-threonine-amide in position 8 resulted in at least a 100-fold loss of receptor binding activity. The classical [D-Ala] substitution for [L-Ala] results in a consistently more potent, presumably more peptidase-resistant, analog than peptide T; amidation of the C terminal threonine also consistently produces somewhat greater potency (FIG. 3).

When the synthetic peptides were tested for their ability to block viral infection of human T cells, experimentors were blind to binding assay results. At $10^{-7}$M the three peptides active in the binding assay are able to reduce detectable levels of reverse transcriptase activity by almost 9-fold. The less active binding displacer [D-Thre]-peptide T similarly showed greatly reduced blockade of viral infection, requiring concentrations 100-fold higher to achieve significant inhibition. Thus, not only the rank order of potencies of the four peptides (D-[Ala]$_1$-peptide T-amide>D-[Ala]$_1$-peptide T>peptide T>D-[Thre]$_8$-peptide T-amide), but also their absolute concentrations in inhibiting receptor binding and viral infectivity are closely correlated (FIG. 3).

EXAMPLE 2

An approximate 60-Kd protein, which is similar if not identical to human T cell T4 antigen, was present in apparently conserved molecular form on membranes prepared from human brain; furthermore, the radiolabeled HIV envelope glycoprotein ($^{125}$I-gp120) can be covalently crosslinked to a molecule present in three mammalian brains whose size and immunoprecipitation properties were indistinguishable from the T4 antigen. Using a method for visualizing antibody-bound receptors on brain slices, the neuroanatomical distribution pattern of brain T4, which is densest over cortical neuropil and analogously organized in all three mammalian brains, was presented. Also, radiolabeled HIV viral envelope glycoprotein bound in an identical pattern on adjacent brain sections, once again suggesting that T4 was the HIV receptor.

EXAMPLE 3

Chemical Neuroanatomy, Computer-Assisted Densitometry. Cryostat-cut 25 micron sections of fresh-frozen human, monkey, and rat brain were thaw-mounted and dried onto gel-coated slides and receptors visualized as described by Herkenham and Pert, *J. Neurosci.*, 2: 1129–1149 (1982). Incubations, with or without antibodies (10 μg/ml) against T4, T4A, T8 and T11, were conducted overnight at 0° C. in RPMI, crosslinked onto their antigens and visualized with $^{125}$I-goat anti-mouse antibody. Incubations of slide-mounted tissue sections in order to label antigen/receptor with $^{125}$I- gp120 were conducted in 5 ml slide carriers with ($10^{-6}$M) or without unlabeled gp120 or Mab OKT4A (10 µg/ml) (Ortho Diagnostics) as described above for membranes.

Computer-assisted transformation of autoradiographic film opacity into quantitative color images was performed. Co-exposure of standards of known increments of radioactivity with the monkey brain sections generated a linear plot (4=>0.99) of log O.D. versus cpm from which the relative concentration of radioactivity can be meaningfully extrapolated. Cell staining of brain sections with thionine was performed by classical methods and visualization of receptors overlying stained tissue.

EXAMPLE 4

Experiments have been conducted to determine the distribution of T4 antigen on a rostral to caudal series or coronal sections of squirrel monkey brain. These experiments show that there are detectable levels of T4 monoclonal antibody binding to cytoarchitectonically meaningful areas of the brain stem (e.g., the substantia nigra), but the striking pattern of cortical enrichment is apparent at every level of the neuroaxis. OKT8, a T-lymphocyte directed monoclonal antibody from the same subclass as OKT4, exhibits no observable pattern. Generally, the more superficial layers within the cerebral cortex contain the densest concentrations of the T4 antigen; the frontal and perilimbic cortex overlying the amydala are particularly receptor-rich throughout the deep layers. The hippocampal formation has the densest concentration of receptors in the monkey, rat, and human brain. Dark field microscopy of squirrel monkey sections dipped in photographic emulsion revealed that the band of densest receptor labelling is located within the molecular layers of the dentate gyrus and hippocampus proper (which contain very few neurons). Thus, receptors appear to be rightly distributed over the neuropil (the neuronal extensions of dendrites and axons) or may be localized to a specific subset of unstained astroglial cells.

Evidence of the specificity of the chemical neuroanatomy and results showing that T4 and the viral envelope recognition molecule are indistinguishable has been determined. Coronal sections of rat brain revealed a very similar cortex/hippocampus-rich pattern of receptor distribution whether OKT4 or $^{125}$I-gp120 was used for visualization. Furthermore, this pattern was not apparent when incubation occurred in the presence of unlabeled gp120 (1 µM), OKT4A (10 µg/ml) or OKT4 (10 µg/ml). Other mouse Mabs directed against other human T cell surface antigens including OKT8 and OKT11 gave no detectable pattern on rat brain when visualized by $^{125}$I-goat anti-mouse IgG secondary antibody just as there was no reproducible, detectable antigen/receptor with secondary antibody alone.

What is claimed:

1. A test kit for detecting antibodies to antigen which bind to a T4 receptor, the test kit containing an antigenic peptide bound to a porous surface or solid substrate, the peptide selected from peptides of the formula:

$R_a$-Ser-Thr-Thr-Thr-Asn-Tyr-Rb or $R^1$-$R^2$-$R^3$-$R^4$-$R^5$ wherein $R_a$ is selected from the group consisting of amino terminal residue Ala- and D-Ala;

Rb is selected from the group consisting of carboxy terminal residue -Thr, -Thr amide and -Thr-Cys, $R^1$ is Thr-;

$R^2$ is selected from the group consisting of Thr and Asp;

$R^3$ is selected from the group consisting of Thr, Ser and Asn;

$R^4$ is Tyr;

$R^5$ is selected from the group consisting of carboxy terminal residue -Thr, -Thr amides and -Thr-Cys.

2. The test kit of claim 1 wherein the peptide is selected from the group consisting of:

D-Ala-Ser-Thr-Thr-Thr-Asn-Tyr-Thr; and

D-Ala-Ser-Thr-Thr-Thr-Asn-Tyr-Thr-amide.

3. The test kit of claim 1, wherein the peptide is selected from the group consisting of:

Thr-Asp-Asn-Tyr-Thr;

Thr-Thr-Ser-Tyr-Thr;

Thr-Thr-Asn-Tyr-Thr and amides thereof.

4. The test kit according to claim 1, wherein the selected peptide is of the formula Ala-Ser-Thr-Thr-Thr-Asn-Tyr-Thr.

5. The test kit according to claim 1, wherein the selected peptide is of the formula Cys-Thr-Thr-Asn-Tyr-Thr-Cys.

6. A kit of claim 1 wherein the antigenic peptide is bound to wells of a microtiter plate.

* * * * *